(12) United States Patent
Zimenkov et al.

(10) Patent No.: US 11,963,931 B2
(45) Date of Patent: Apr. 23, 2024

(54) CONTAINER FOR BLOOD COMPONENT COOLING AND FREEZING

(71) Applicant: Haemonetics Corporation, Boston, MA (US)

(72) Inventors: Yuri Zimenkov, Cambridge, MA (US); Bruno Piazzarolo, Waltham, MA (US); Dinesh Kommireddy, Derry, NH (US); Shinji Yue, Westford, MA (US); Tim Fallon, Dover, MA (US)

(73) Assignee: Haemonetics Corporation, Boston, MA (US)

( * ) Notice: Subject to any disclaimer, the term of this patent is extended or adjusted under 35 U.S.C. 154(b) by 891 days.

(21) Appl. No.: 15/110,847

(22) PCT Filed: Jan. 13, 2015

(86) PCT No.: PCT/US2015/011195
§ 371 (c)(1),
(2) Date: Jul. 11, 2016

(87) PCT Pub. No.: WO2015/106267
PCT Pub. Date: Jul. 16, 2015

(65) Prior Publication Data
US 2016/0331636 A1    Nov. 17, 2016

Related U.S. Application Data

(60) Provisional application No. 61/926,890, filed on Jan. 13, 2014.

(51) Int. Cl.
| | |
|---|---|
| *A61J 1/16* | (2023.01) |
| *A61J 1/05* | (2006.01) |
| *A61M 1/34* | (2006.01) |

(52) U.S. Cl.
CPC .......... *A61J 1/165* (2013.01); *A61J 1/05* (2013.01); *A61M 1/3496* (2013.01)

(58) Field of Classification Search
CPC .... A61M 1/3496; A61M 1/0272; A61M 5/44; A61J 1/165; A61J 1/05; F25D 2400/28; F25D 2400/30; B65D 81/00
(Continued)

(56) References Cited

U.S. PATENT DOCUMENTS

| | | |
|---|---|---|
| 3,158,283 A * | 11/1964 | Rinfret ............... A23L 3/364 165/133 |
| RE31,688 E | 9/1984 | Popovich et al. |

(Continued)

OTHER PUBLICATIONS

International Search Authority/US—International Search Report and the Written Opinion, International Application No. PCT/US2015/011195, 8 pages, dated May 1, 2015.

*Primary Examiner* — Andrew J Mensh
(74) *Attorney, Agent, or Firm* — Nutter McClennen & Fish LLP

(57) ABSTRACT

A blood component cooling container includes a body portion having a proximal end and a distal end. The body portion defines an interior volume, and includes a plurality of cooling vanes that extend radially outward from the body portion. The cooling vanes increase the external surface area of the blood component cooling container. The blood component cooling container also has an opening within the body portion and configured to receive collected plasma.

21 Claims, 14 Drawing Sheets

(58) Field of Classification Search
USPC .......................................................... 604/403
See application file for complete search history.

(56) References Cited

U.S. PATENT DOCUMENTS

| | | | |
|---|---|---|---|
| 4,731,072 A | | 3/1988 | Aid |
| 4,755,300 A | * | 7/1988 | Fischel .................. B01D 63/16 |
| | | | 210/321.68 |
| 5,297,234 A | | 3/1994 | Harms et al. |
| 5,364,385 A | * | 11/1994 | Harms ...................... A61J 1/05 |
| | | | 604/403 |
| 2002/0081401 A1 | * | 6/2002 | Hessok ................ B65D 1/0276 |
| | | | 428/34.1 |
| 2004/0129003 A1 | * | 7/2004 | Voute ................... A01N 1/0263 |
| | | | 220/592.28 |
| 2008/0314052 A1 | | 12/2008 | Shin |
| 2012/0304597 A1 | * | 12/2012 | Mikhailov .............. B67B 7/182 |
| | | | 53/287 |
| 2015/0138519 A1 | * | 5/2015 | Luijten .................. H05G 2/008 |
| | | | 250/504 R |

* cited by examiner

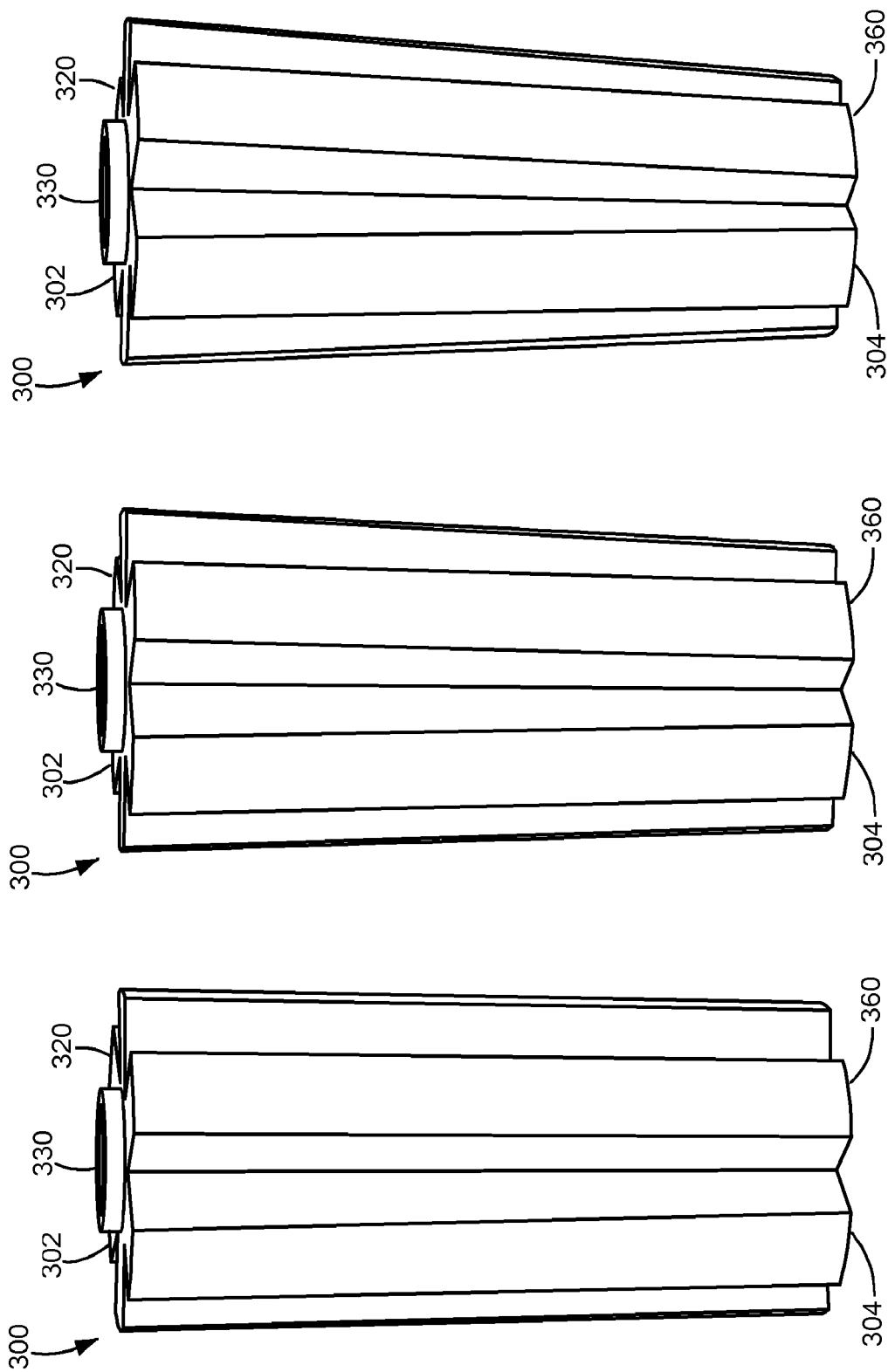

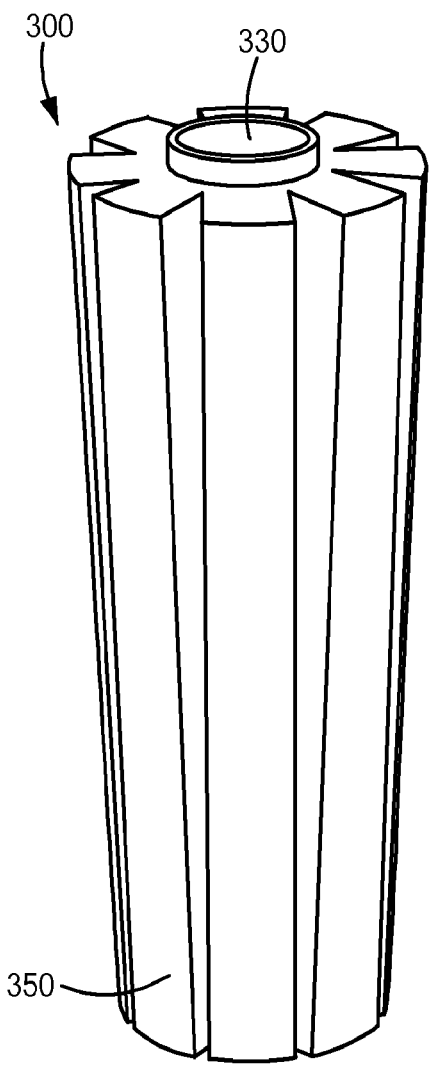 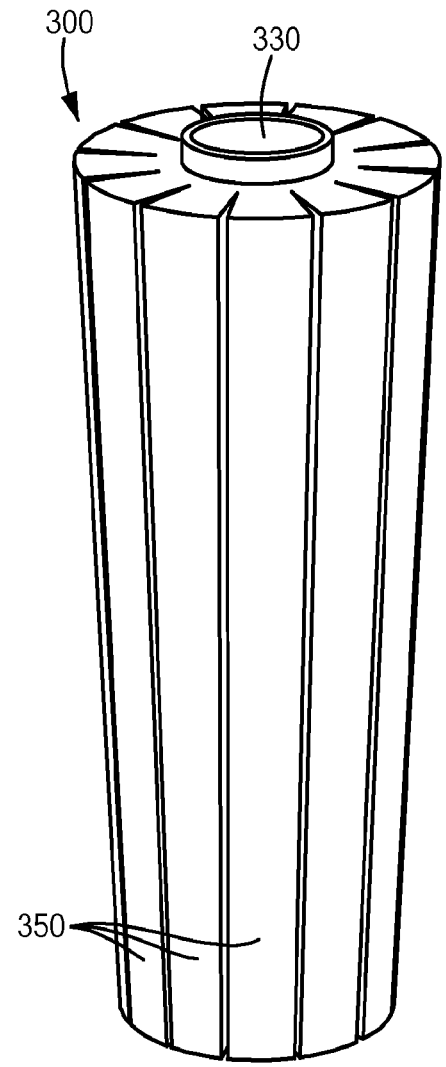
*FIG. 5D*  *FIG. 5E*

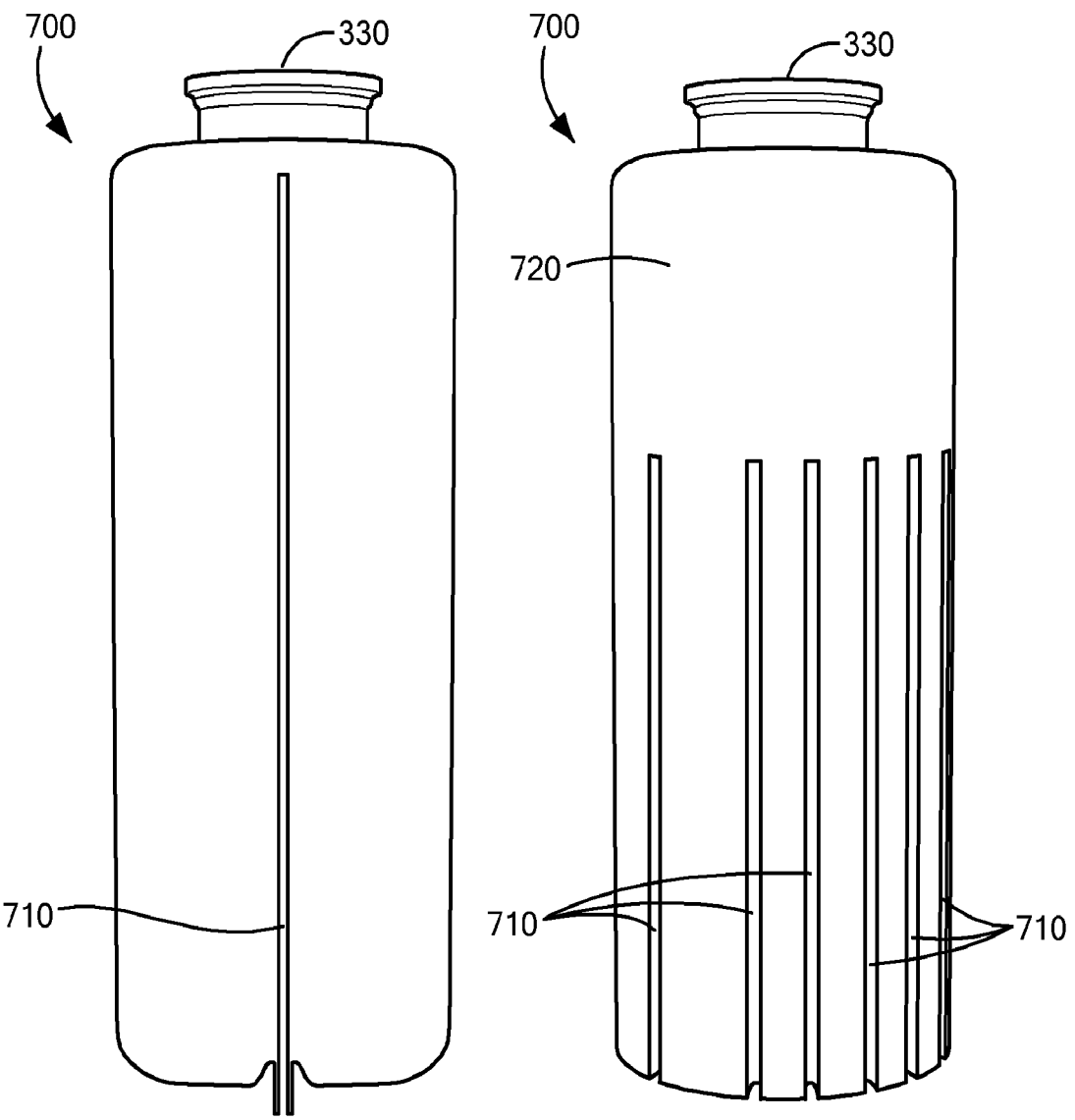
*FIG. 7A*  *FIG. 7B*

CONTAINER FOR BLOOD COMPONENT COOLING AND FREEZING

PRIORITY

This patent application claims priority from U.S. Provisional Patent Application No. 61/926,890, filed Jan. 13, 2014, entitled, "A Container for Blood Component Cooling and Freezing," and naming Yuri Zimenkov, Bruno Piazzarolo, Dinesh Kommireddy, Shinji Yue, and Tim Fallon as inventors, the disclosure of which is incorporated herein, in its entirety, by reference.

TECHNICAL FIELD

The present invention relates to blood component storage containers, and more particularly to blood component containers in which blood components (e.g., plasma) may be stored, cooled, and/or frozen.

BACKGROUND ART

After human plasma is collected (e.g., during a blood apheresis procedure), some components of the collected plasma begin to degrade with time. Temperature is one of the main factors in the plasma degradation. Therefore, to help reduce degradation, fresh plasma that is collected for commercial fractionation may be stored in bottles similar to those shown in FIGS. 1A and 1B, and placed into a freezing room. By freezing the collected plasma, the degradation of the various components of the plasma (e.g., Coagulation Factors such as Factor V and Factor VIII) may be reduced. As shown in FIGS. 1A and 1B, some prior art plasma bottles have a cylindrical shape and a substantially smooth outer surface to facilitate automated handling of the plasma bottles 100.

SUMMARY OF THE EMBODIMENTS

In a first embodiment of the invention there is provided a blood component cooling and/or freezing container that has a body portion and an opening within the body portion. The body portion has a proximal end and a distal end, and defines an interior volume. The body portion also includes a plurality of cooling vanes extending radially outward from the body portion. The cooling vanes increase the external surface area of the blood component cooling and/or freezing container. The opening is configured to receive collected plasma.

The plurality of cooling vanes may include two cooling vanes, four cooling vanes, five cooling vanes, six cooling vanes, eight cooling vanes, or twelve cooling vanes. Each of the cooling vanes may define a vane internal volume, and the interior volume of the blood component cooling container may include the vane internal volume(s). Additionally or alternatively, each of the cooling vanes may be curved such that the blood component cooling container has a generally cylindrical shape. The blood component cooling container may be tapered from the distal end to the proximal end, such that the diameter of the proximal end is greater than the diameter of the distal end.

In some embodiments, the blood component cooling and/or freezing container may include a flexible metallic frame located on the external surface of the blood component cooling and/or freezing container. The flexible metallic frame may improve the heat exchange properties of the blood component cooling and/or freezing container, and may contact the bottom and/or sides of the blood component cooling and/or freezing container.

In accordance with further embodiments, a method for storing plasma may include introducing plasma into a blood component cooling and/or freezing container and transferring the blood component cooling and/or freezing container to a freezer. The blood component cooling and/or freezing container may include (1) an opening for receiving the plasma, and (2) a body portion that has a proximal end and a distal end and defines an interior volume. The body portion may include a plurality of cooling vanes extending radially outward from the body portion. The plurality of cooling vanes may increase the external surface area of the blood component cooling container, and may reduce the freezing time of the plasma within the blood component cooling container.

In some embodiments, the plasma may be collected during a plasmapheresis procedure, and introducing the plasma into the blood component cooling and/or freezing container may include transferring plasma from a blood component separation device to the blood component cooling container. The blood component cooling and/or freezing container may be tapered from the distal end to the proximal end. In other embodiments, the method may also include removing the blood component cooling and/or freezing container from the freezer, defrosting the blood component cooling and/or freezing container, opening the blood component cooling and/or freezing container (e.g., using an automatic bottle opener), and removing the plasma from the bottle. The plurality of cooling vanes may reduce the defrosting time of the plasma within the blood component cooling container. The taper may prevent frozen plasma from getting stuck inside the blood component cooling container.

In accordance with further embodiments, a blood component cooling container may include a body portion that has a proximal end and a distal end, and defines an interior volume. The container may also include at least one convection member that is spaced about the body portion, and an opening within the body portion that is configured to receive collected plasma. The convection member(s) may increase the external surface area of the blood component cooling container.

In some embodiments, the convection member(s) may include a plurality of cooling vanes (e.g., two, four, five, or six cooling vanes). Each of the cooling vanes may include an internal vane volume, and the interior volume of the blood component cooling container may include the internal vane volume(s). In other embodiments, the convection member(s) may include one or more slits within body portion and/or indent(s) within body portion. Additionally or alternatively, the blood component cooling container may be tapered from the distal end to the proximal end (e.g., such that the diameter of the proximal end is greater than the diameter of the distal end).

The blood component cooling container may also include a flexible metallic frame that is located on the external surface of the blood component cooling container. The flexible metallic frame may improve the heat exchange properties of the blood component cooling container, and may contact the bottom and/or sides of the blood component cooling container. In some embodiments, the blood component cooling container may have a generally cylindrical shape such that the blood component cooling container may be opened using an automatic bottle opener.

BRIEF DESCRIPTION OF THE DRAWINGS

The foregoing features of embodiments will be more readily understood by reference to the following detailed description, taken with reference to the accompanying drawings, in which:

FIGS. 4A-4C schematically show side views of alternative embodiments of a blood component cooling and/or freezing container, in accordance with additional embodiments of the present invention.

FIGS. 5A-5E schematically show side views of additional alternative embodiments of a blood component cooling and/or freezing container having varying numbers of cooling vanes, in accordance with additional embodiments of the present invention.

FIGS. 7A-7B schematically show side views of additional alternative embodiments of a blood component cooling and/or freezing container, in accordance with further embodiments of the present invention.

DETAILED DESCRIPTION OF SPECIFIC EMBODIMENTS

Figure 2:
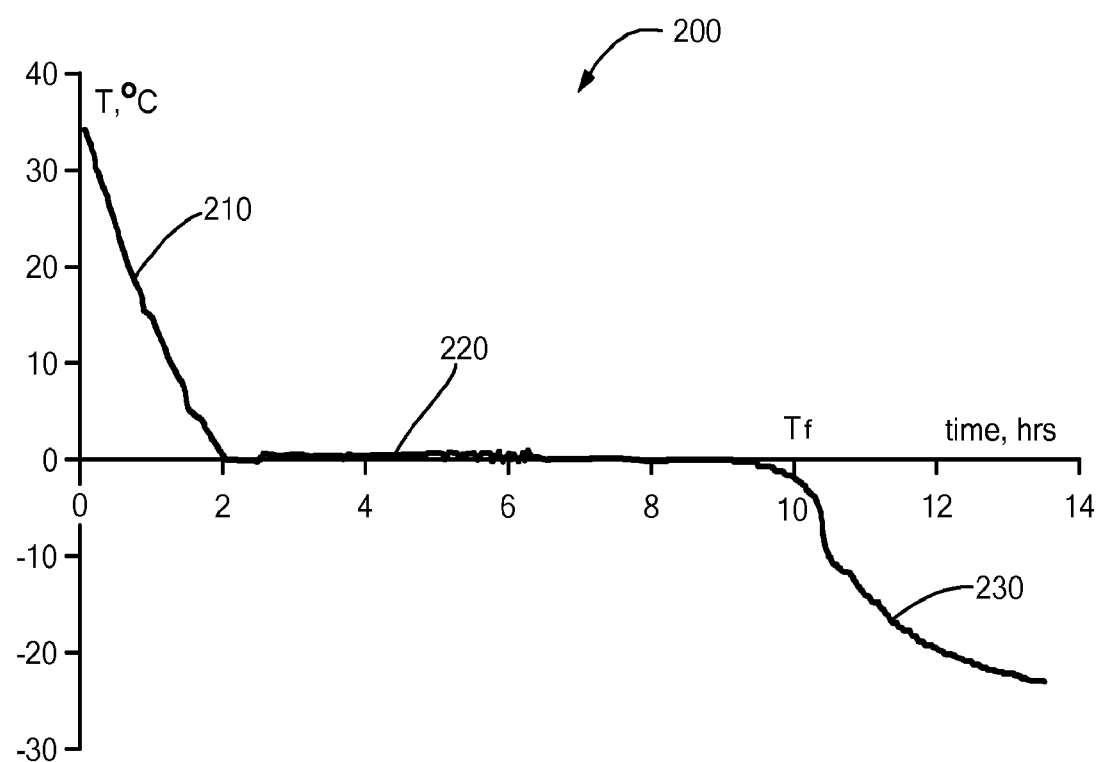
FIG. 2 schematically shows a plasma cooling profile for plasma stored in the prior art plasma cooling bottle shown in FIGS. 1A and 1B.

In illustrative embodiments, a blood component cooling and/or freezing container may have various features that help to decrease the overall time required to fully cool/freeze the blood component stored within the container (e.g., by facilitating convective cooling and freezing). For example, as shown in FIG. 2, based upon experimental data, the plasma freezing profile 200 for plasma stored in a prior art bottle (e.g., in the middle of a prior art plasma bottle 100) consists of essentially three stages. The first stage 210 is a relatively quick cooling of the plasma from body temperature (e.g., approximately 37° C.) to 0° C. The second stage 220 is a phase transition (e.g., freezing of the plasma) which begins at the outside of the bottle 100 and progresses inwards towards the center of the bottle. During the final stage 230 of the freezing profile 200, frozen plasma is further cooled to the freezer temperature (e.g., the temperature of the freezer in which the plasma is stored). As discussed in greater detail below, various embodiments of the present invention improve upon this cooling/freezing profile. In this manner, some embodiments of the present invention reduce and/or minimize the degradation of the blood component (and its components). Details of illustrative embodiments are discussed below.

Figure 3A:
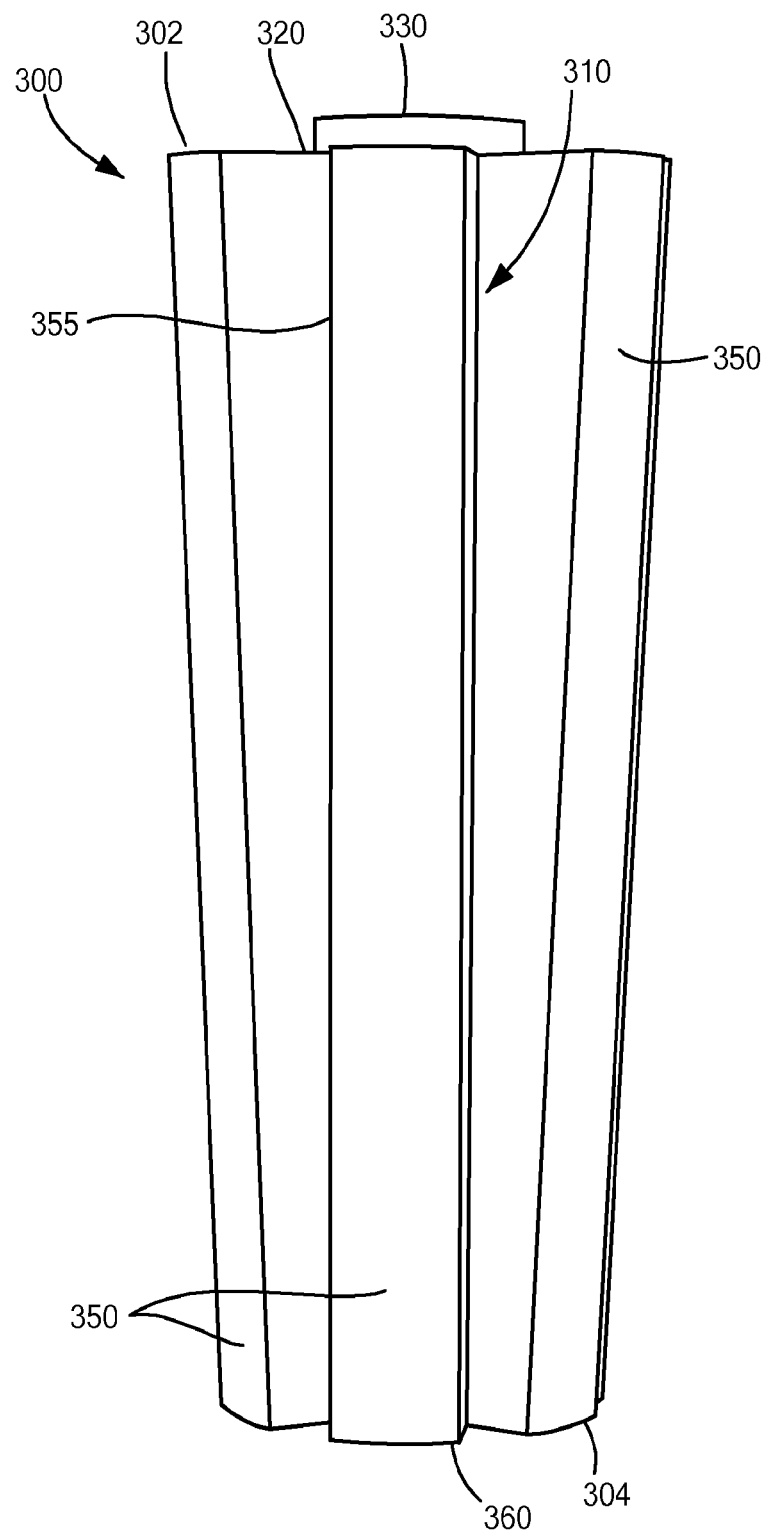
FIG. 3A schematically shows a perspective view of a blood component cooling and/or freezing container, in accordance with some embodiments of the present invention.
Figure 3B:
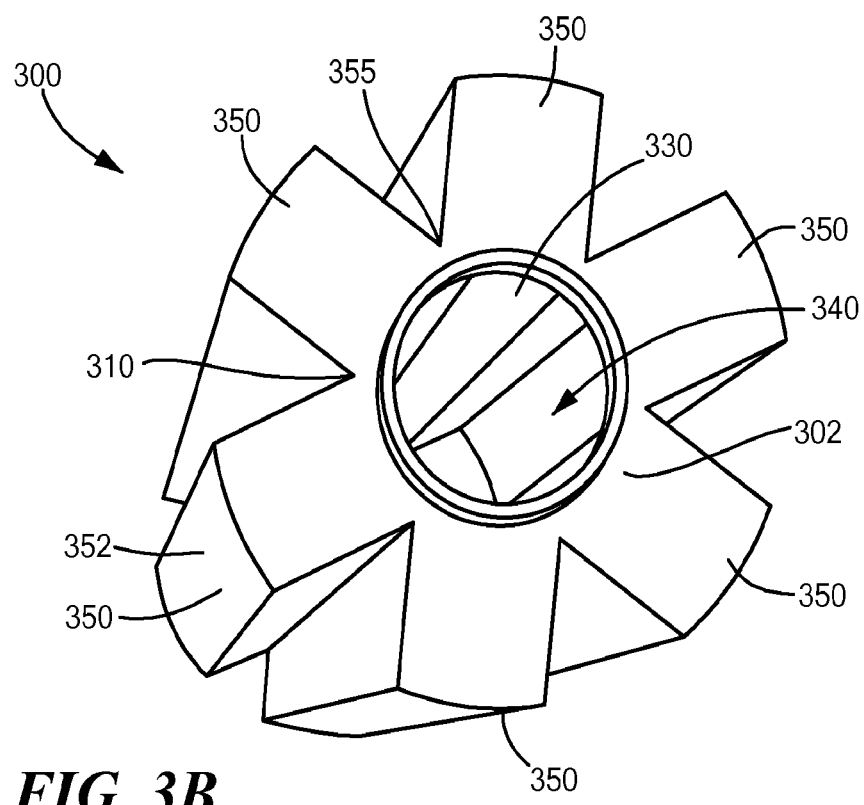
FIG. 3B schematically shows a top view of the blood component cooling and/or freezing container of FIG. 3A, in accordance with some embodiments of the present invention.
Figure 3C:
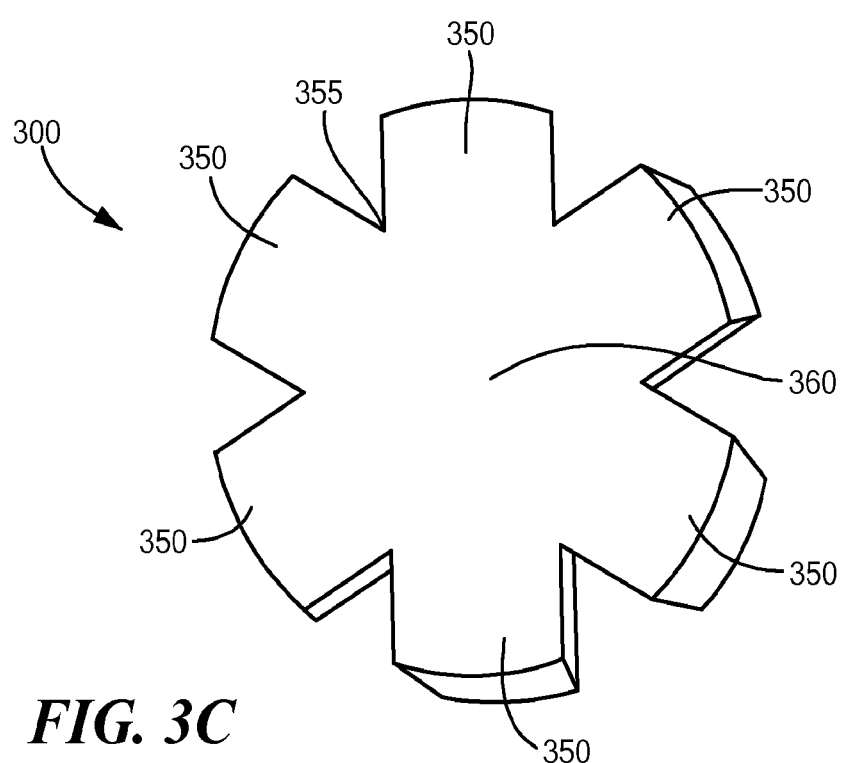
FIG. 3C schematically shows a bottom view of the blood component cooling and/or freezing container of FIG. 3A, in accordance with some embodiments of the present invention.

FIGS. 3A-3C show a blood component cooling and/or freezing container 300 (e.g., a plasma cooling bottle) in accordance with some embodiments of the present invention. The blood component cooling and/or freezing container 300 may have a body portion 310 that defines an interior volume in which plasma (or another blood component) can be stored. To facilitate the transfer of plasma into the container 300, the container 300 may include an opening 330 in the top 320 (e.g., at the proximal end 302 of the blood component cooling and/or freezing container 300). Therefore, once plasma is collected (e.g., into a plasma collection bag during an apheresis process), the technician may transfer the plasma from the plasma collection bag to the container 300 through the opening 330. Alternatively, the plasma may be collected directly into the container 300.

As mentioned above, various embodiments of the present invention can include features that improve plasma cooling within the bottle 300. To that end, the blood component cooling container 300 may include cooling vanes 350 (e.g., convection fins/vanes) that extend outwardly from the body portion 310 of the bottle 300. As discussed in greater detail below, the cooling vanes 350 act to decrease the time required to freeze the plasma (e.g., increase the rate of cooling), for example, by increasing the external surface area of the plasma bottle 300 and/or decreasing the distance from an external surface of the bottle 300 to the center of the bottle 300.

It is important to note that, in order to preserve and/or maximize the internal volume of the blood component cooling and/or freezing container 300, in some embodiments, the cooling vanes 350 may not be solid. For example, as shown in FIG. 3B, the walls of the cooling vanes 350 may have a similar thickness to the wall thickness of the rest of the body portion 310 (e.g., the main body portion), such that the cooling vanes are not solid structures and define an interior volume within each of the vanes 350. In this manner, the interior volume 340 of the container 300 (e.g., the volume of the main body portion and the volume within each of the vanes 250) may have a shape similar to the cross-sectional shape of the bottle 300 (e.g., the interior volume 340 and the cross-sectional shape of the bottle 300 may be "star-shaped" or "asterisk-shaped").

Figure 1A:
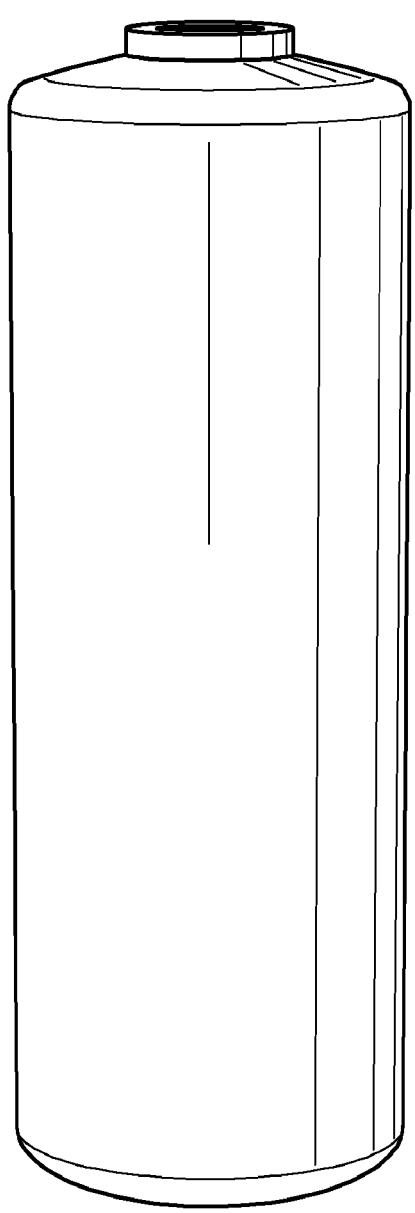
FIG. 1A schematically shows a perspective view of a prior art plasma storage bottle.
Figure 1B:
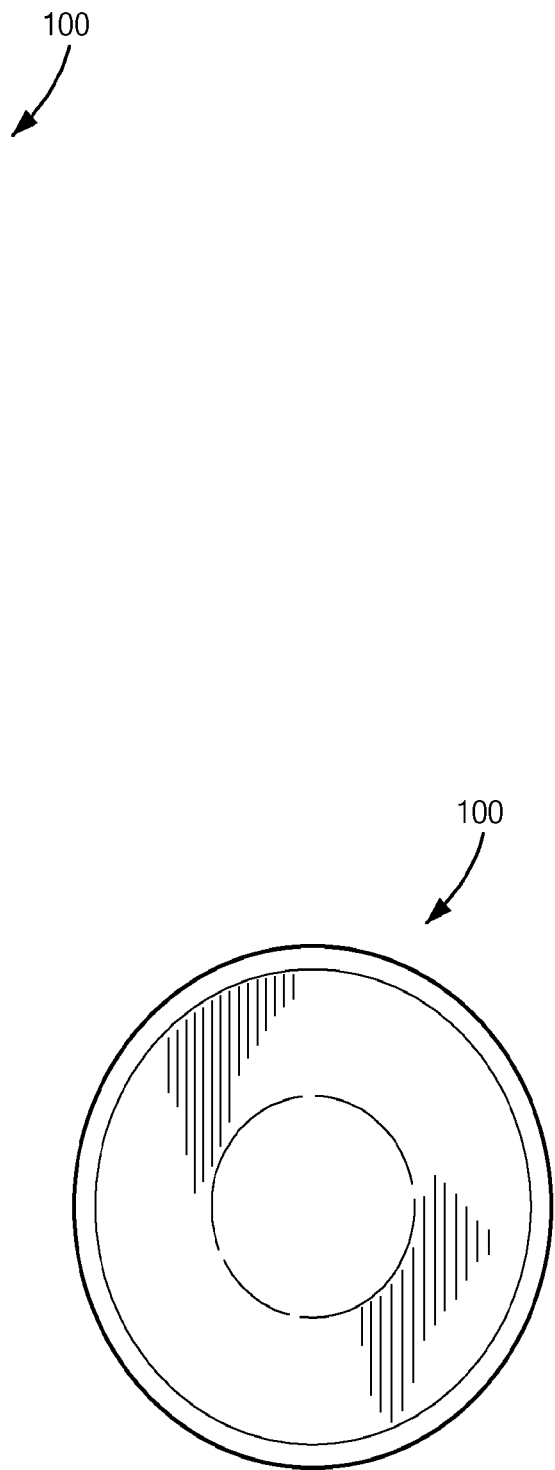
FIG. 1B schematically shows a bottom view of the prior art plasma storage bottle.

As mentioned above, many prior art plasma bottles (e.g., the bottle 100 shown in FIGS. 1A and 1B) have a generally cylindrical shape. Therefore, as one may expect, much of the handling equipment used during processing (e.g., automatic bottle openers, etc.) is designed to handle cylindrical containers. Therefore, in order to avoid the need to replace existing equipment, the outer surface 352 of the cooling vanes 300 may be curved to allow the blood component cooling and/or freezing container 300 to have a generally circular/cylindrical shape (FIG. 3C). By having a generally circular/cylindrical shape, some embodiments of the blood component cooling and/or freezing container 300 are compatible with existing processing and handling equipment (e.g., automatic bottle openers) currently used with the prior art plasma bottle 100 shown in FIGS. 1A and 1B.

After the plasma is stored (e.g., within the container 300) for a period time and prior to use, the container 300 may be removed from the freezer, the plasma allowed to thaw (completely thaw or partially thaw), and the container 300 may be opened, for example, using the automatic bottle opening mentioned above. Once the container 300 is opened, the plasma may be removed for further processing. However, in some prior art containers, a portion of the plasma (e.g., some of the still frozen plasma) may get stuck within the bottle/container 300. To avoid this issue, some embodiments of the blood component cooling and/or freezing container 300 may be tapered from the bottom 360 (e.g., the distal end 304) of the blood component cooling container 300 to the top 320 (e.g., the proximal end 302). In other words, the cross-sectional diameter of the distal end 304 of bottle may be smaller than the diameter of proximal end 302, and the blood component cooling container 300 may gradually widen (e.g., the cross-sectional diameter of the blood component cooling and/or freezing container 300 may gradually increase) from the bottom 360 of the bottle 300 to the top 320 of the bottle 300. This taper helps to ensure that bottle 300 can be substantially completely emptied (e.g., after being opened by an automatic bottle opener), for example, by minimizing the likelihood that the frozen plasma will get stuck inside the bottle 300 during emptying.

It is important to note that the type and extent of the taper can depend on the intended application and the volume of the container 300. Therefore, as shown in FIGS. 4A-4B, some embodiments may have different tapers from that shown in FIGS. 3A-3C. For example, some embodiments may have no taper (e.g., the container has the same cross-sectional diameter along its length, FIG. 4A), while some embodiments may have an intermediate/slight taper (FIG. 4B), and some embodiments may have a greater taper (FIG. 4C) than that shown in FIGS. 3A-3C.

To further improve the plasma removal (e.g., the removal of a frozen plasma slug from the container), the inner walls (e.g., the inner walls of the body portion 310 and/or the inner walls of the vanes 350) may include a coating that helps the frozen plasma slide out of the opened container 300. For example, in some embodiments, the inner walls of the container 300 and/or vanes 350 may be coated with Teflon (or similar non-stick material). Although coatings other than Teflon may be used, it is important to note that, because the coating may contact the stored blood component, the coating should be compatible with the material (e.g., plasma) stored within the container 300.

Figure 5C:
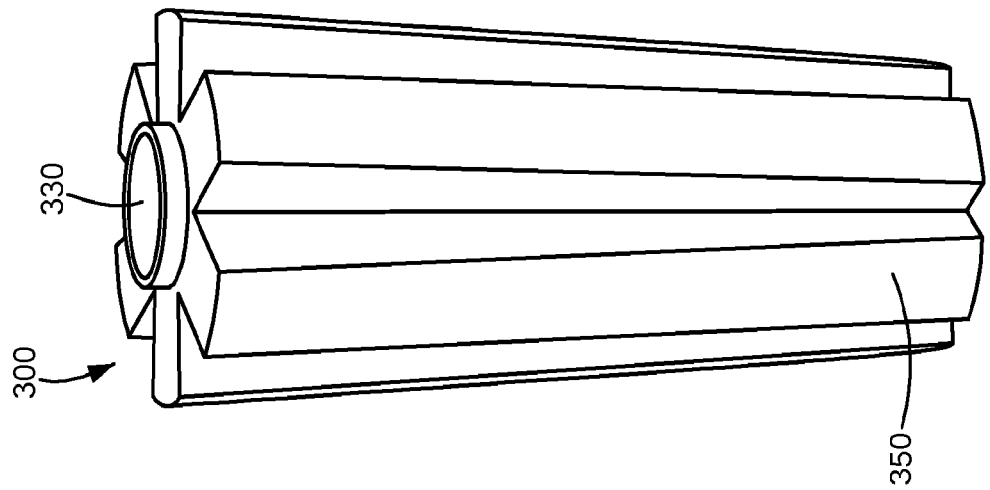
Figure 5B:
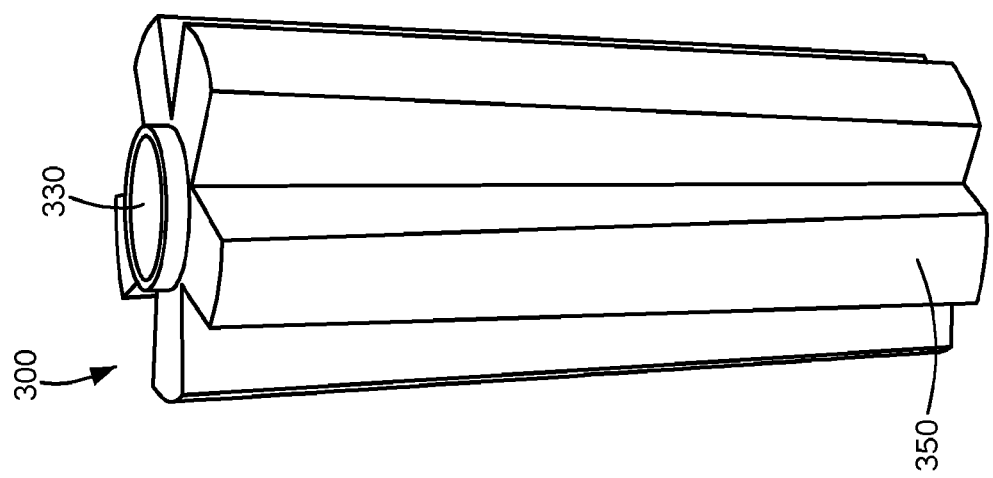
Figure 5A:
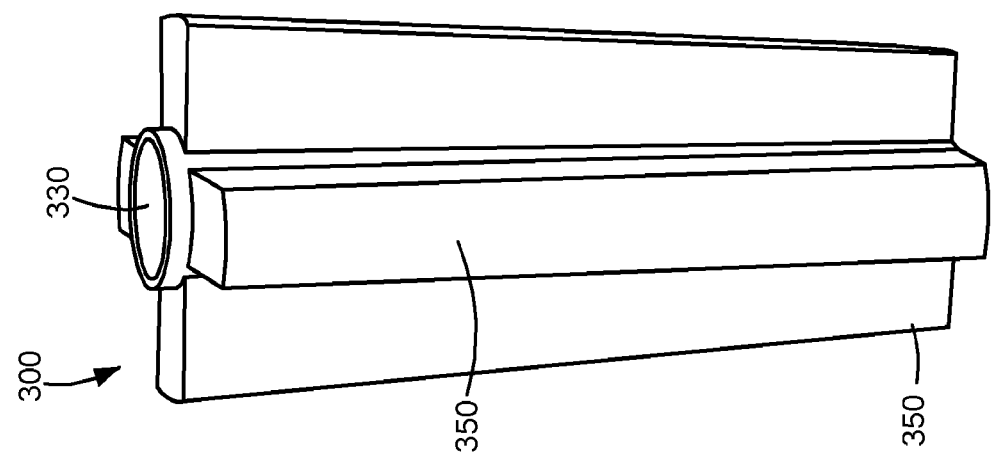

Although the embodiment shown in FIGS. 3A-3C (and FIGS. 4A-4C) have six cooling vanes 350 equally spaced about the diameter of the bottle 300, the number and the configuration of the vanes 350 can vary, for example, based upon the application, the anticipated material that will be stored within the container 300, and/or the required cooling/freezing time and/or temperature. For example, as shown in FIGS. 5A-5E, the blood component cooling and/or freezing container may have more or less than six cooling vanes 350. In some embodiments, the blood component cooling container 300 may have four vanes 350 (FIG. 5A), five vanes 350 (FIG. 5B), eight vanes 350 (FIG. 5D), or twelve vanes 350 (FIG. 5E). It should be noted that these are only provided as examples of the number of vanes 350, and some embodiments may have less than four vanes 350, seven vanes 350, between nine and eleven vanes 350, or more than twelve vanes 350.

Furthermore, the vanes 350 do not need to be equally spaced about the cooling bottle 300, and do not need to extend the length of the bottle 300 (e.g., they may only extend along part of the bottle 300). For example, the vanes 350 may be unevenly spaced around the outer periphery of the bottle 300. Additionally or alternatively, some or all of the vanes 350 may only extend part way along the length of the container 300 (e.g., the vanes 350 may only extend half way, a quarter of the way, or three-quarters of the way along the length of the container 300).

As mentioned above, various embodiments of the present invention and the cooling vanes 350 described above decrease the time required to freeze the plasma within the bottle 300. To that end, the cooling vanes 350 act to significantly increase the surface area of the container (e.g., the surface area of the outer surface of the container 300 and/or the surface area of the inner surface of the container 300). For example, the six-vane embodiment shown in FIGS. 3A-3C has approximately twice the surface area of the standard blood component cooling container 100 shown in FIG. 1A. This increased surface area, in turn, significantly reduces the overall freezing time. Additionally, the cooling vanes 350 also create areas 355 in which the distance from the center of the container 300 to the outer wall is reduced. This helps to further reduce the cooling/freezing time.

Figure 6:
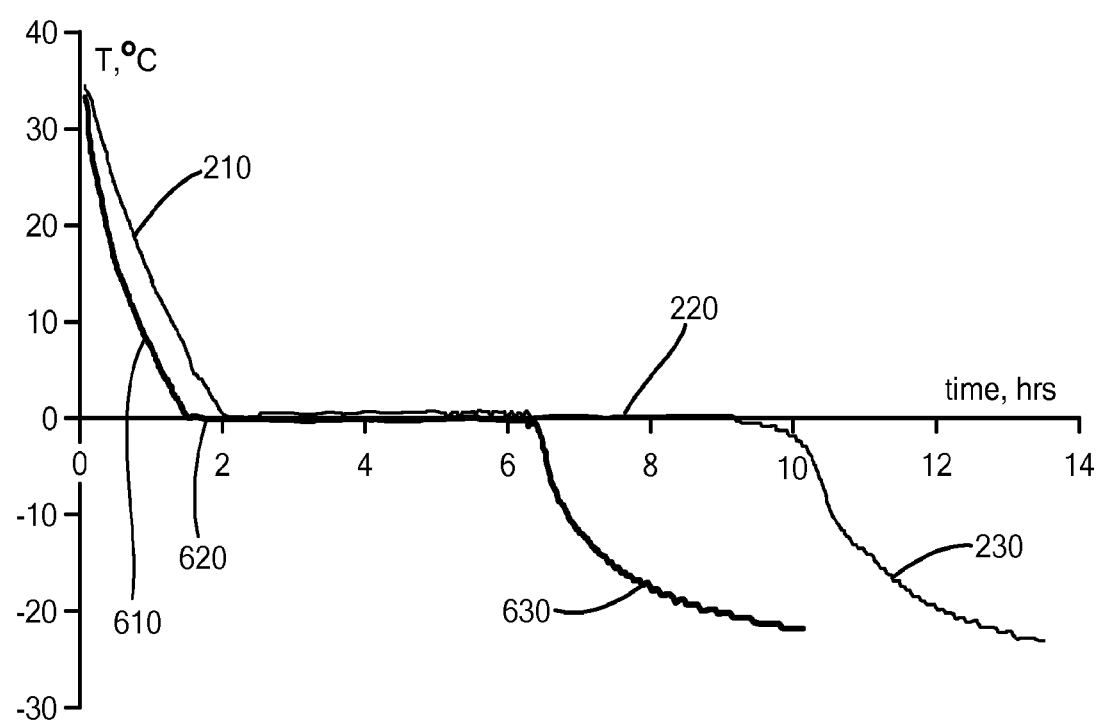
FIG. 6 schematically shows a plasma cooling profile for plasma stored in the prior art blood component cooling and/or freezing container shown in FIGS. 1A and 1B as compared to a blood component cooling and/or freezing container in accordance with embodiments of the present invention.

FIG. 6 shows an exemplary cooling/freezing profile 600 of some embodiments of the present invention as compared to the cooling/freezing profile 200 of a standard/prior art plasma bottle 100. As shown in FIG. 6, the presence of the vanes 350 decreases (e.g., by approximately 40%) the time of each stage of freezing (e.g., cooling of the plasma from body temperature to 0° C. 210/610, the phase transition/freezing of the plasma 220/620, and further cooling to the freezer temperature 230/630) as compared to prior art containers 100. In this manner, embodiments of the present invention can reduce the time required to both cool the plasma (e.g., stage 610 in FIG. 6) and freeze the plasma (e.g., stages 620/630 of FIG. 6). As discussed above, this, in turn, helps reduce the degradation of the plasma and the plasma components.

It is important to note that, in addition to increasing the external surface area of the cooling and/or freezing bottle 300, the cooling vanes 350 also provide additional benefits that can aid in the reduction of freezing time (e.g., increasing the rate of cooling and freezing). For example, in some embodiments, the cooling vanes 350 may increase the structural strength of the bottle 300. The increased strength may allow the bottles 300 to have thinner wall thicknesses than the prior art bottle 100 shown in FIG. 1. The reduced wall thickness, in turn, can improve temperature transfer, further improve cooling, and reduce the time required to fully freeze the plasma.

In addition to the cooling vanes 350 (which increase the external surface area of the blood component cooling container 300), some embodiments may have additional features that improve cooling/freezing time. For example, some embodiments may include a flexible metallic frame (not shown) that contacts (e.g., partially or fully contacts) the bottom 360 and/or sides of the blood component cooling container 300. The flexile metallic frame may further improve the heat exchange characteristics/properties of the blood component cooling and/or freezing container 300.

The metallic frame can be located on the outside of the container 300 (e.g., it can be a sleeve that fits over the outside of the container 300) or the frame may be located within the container 300 (e.g., the frame can be an insert within the container 300). Additionally or alternatively, the frame may be formed within the walls of the container 300. For example, the wall of the container 300 may be formed around the frame such that the frame is not exposed to the outside atmosphere or the internal contents of the container 300. It is important to note that, if the frame is positioned such that it may contact the contents of the container 300 (e.g., plasma), a frame material should be selected that is both compatible with and approved for use with plasma.

Although the blood component cooling and/or freezing container 300 shown in FIGS. 3A-3C and described above has cooling vanes 350 to help improve cooling/freezing, other embodiments may include additional or alternative features to reduce the freezing time. For example, as shown in FIGS. 7A and 7B, the blood component cooling and/or freezing container 700 may have slits 710 along the length of the container 700. Like the cooling vanes 350 discussed above, the slits 710 increase the external surface area of the bottle 700 and decrease the time required to fully freeze the plasma. The bottle 700 can have any number of slits 710. For example, the bottle may have one slit 710, two slits 710 (e.g., one on either side of the bottle 700; FIG. 7A) or more than two slits 710 (FIG. 7B).

It should also be noted that the slits 710 can have varying thicknesses. For example, as shown in FIGS. 7A and 7B, the slits 710 can be relatively thin (FIG. 7A) or may be thicker/wider (FIG. 7B) (e.g., the slits in FIG. 7A are thinner than those shown in FIG. 7B). Additionally or alternatively, as shown in FIG. 7B, in some embodiments, the slits 710 need not be spaced evenly about the diameter of the bottle/container 700. In such embodiments, the slits 710 may be concentrated within a certain area on the bottle, for example, to increase the surface area in a specific region. Furthermore, in some embodiments, the container/bottle 700 may have a combination of thinner and thicker slits 710.

As also shown in FIG. 7B, like the vanes 350 discussed above, in some embodiments, the slits 710 may only extend part way along the length of the bottle 700. For example, the slits 710 may extend half or three quarters the way up the bottle 710 leaving a portion 720 of the bottle 700 (e.g., near the top of the bottle 700) without slits 710. This may allow existing handling equipment to more easily handle the bottle 700 and provide a smooth surface where the automatic bottle opener can open the bottle 700.

Figure 8C:
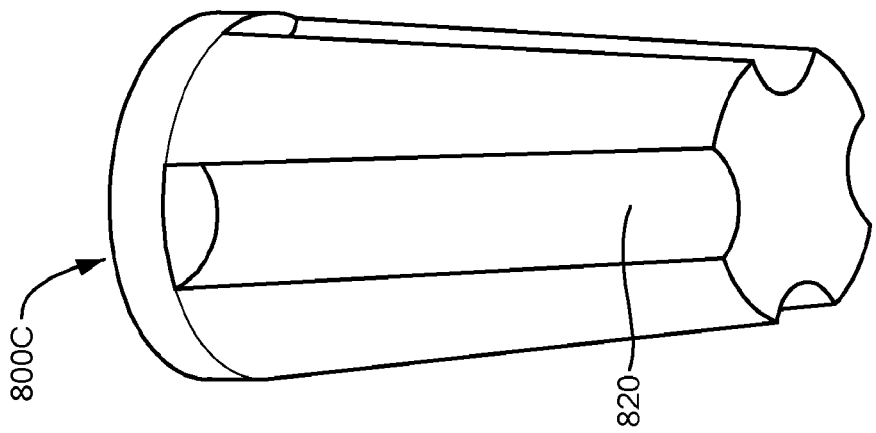
FIGS. 8A-8J schematically show further alternative embodiments of blood component cooling and/or freezing containers in accordance with additional embodiments of the present invention.
Figure 8B:
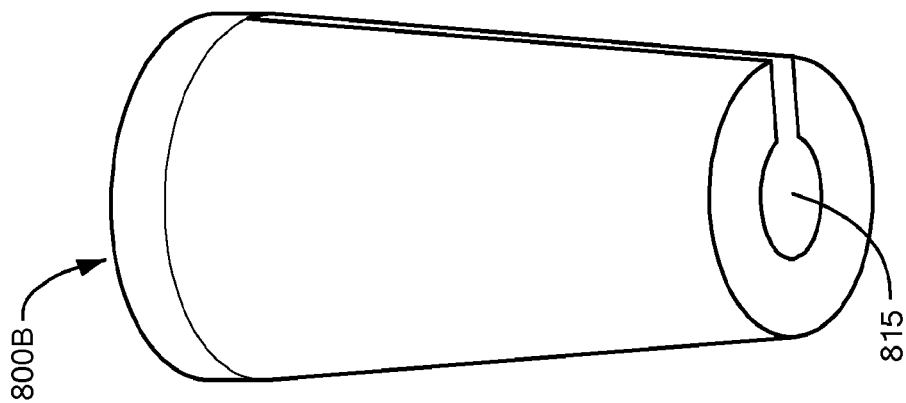
Figure 8A:
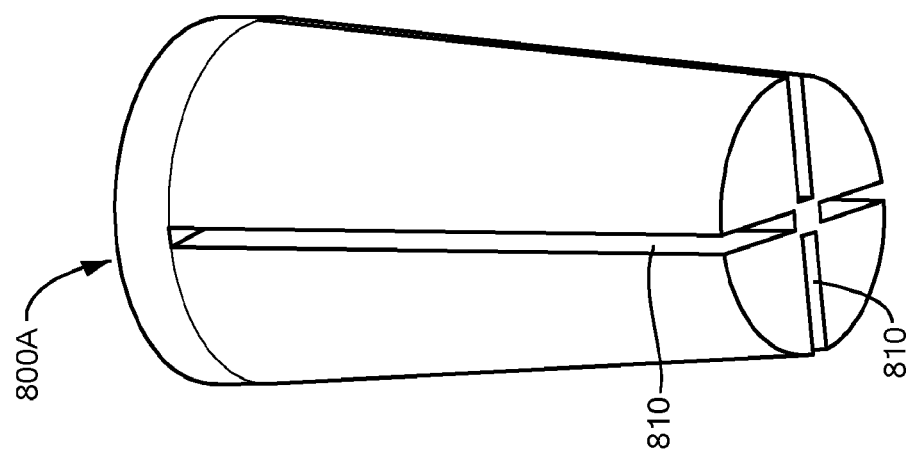
Figure 8F:
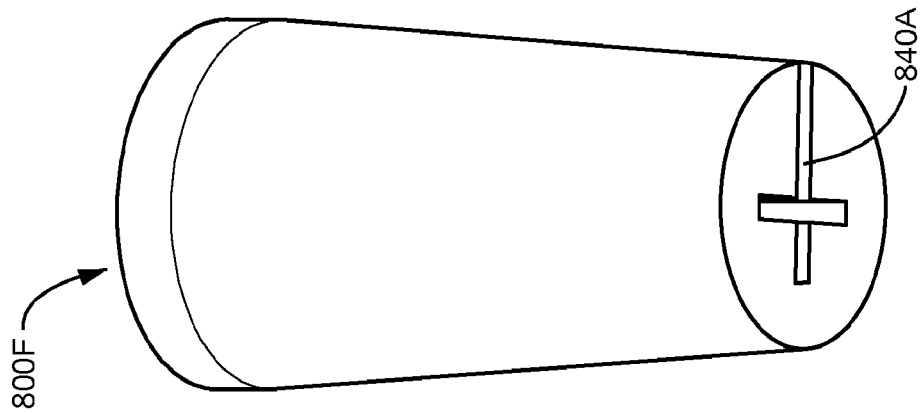
Figure 8E:
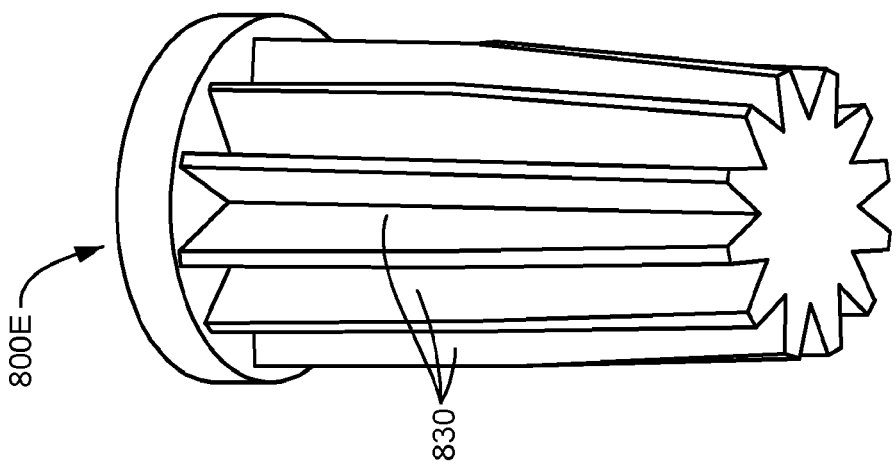
Figure 8D:
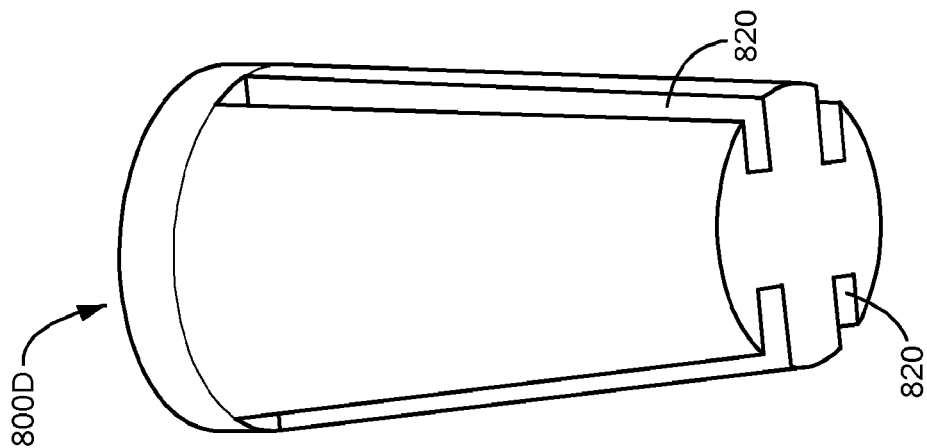
Figure 8G:
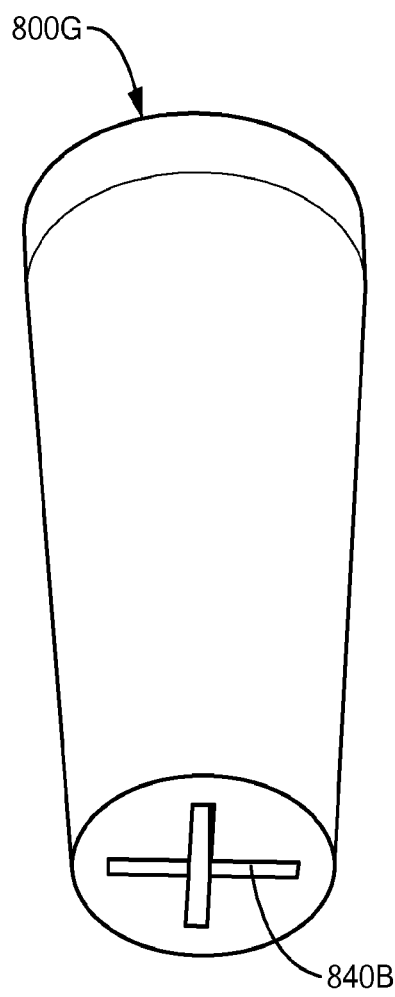
Figure 8H:
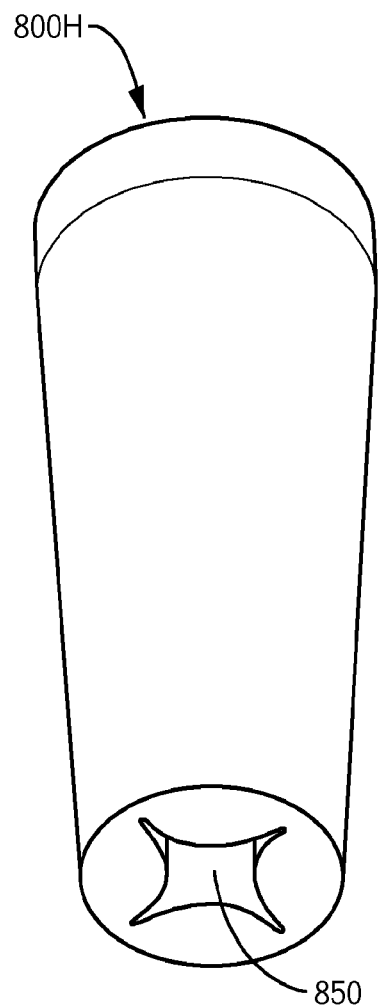
Figure 8I:
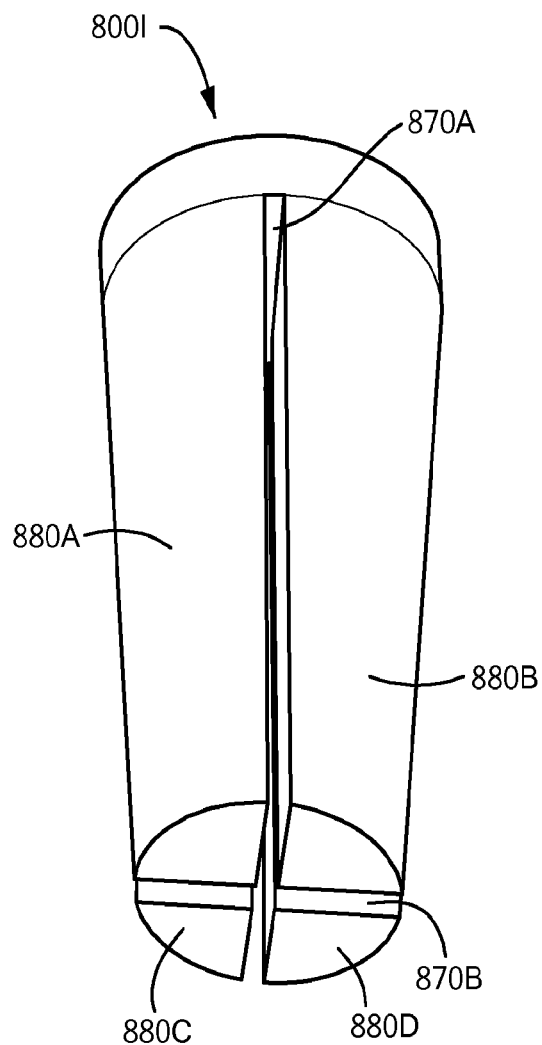
Figure 8J:
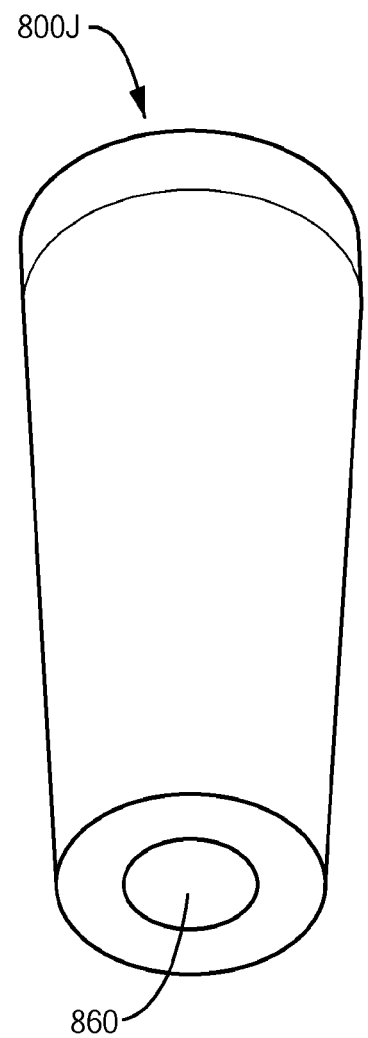

FIGS. 8A-8J show several alternative embodiments of blood component cooling and/or freezing containers 800A-800J with various alternative features that improve plasma cooling/freezing (e.g., increase the rate of cooling/freezing). For example, FIGS. 8A and 8I show blood component cooling and/or freezing containers 800A/800I with slits 810/870A/B similar to those shown in FIGS. 7A and 7B. As shown in FIG. 8A, the slits 810 may extend only part way through the diameter of the bottle 800A. Alternatively, the indents/slits 870A/B can extend through the diameter of the bottle 800I such that the bottle 800I is divided into four compartments 880A-880D in which the plasma may be collected/stored.

Additionally or alternatively, as shown in FIGS. 8B, 8F-8H, and 8J, in some embodiments, the bottle/container may have an open internal core. For example, some containers 800B may have a C-shaped cross-section that creates an open core 815. Alternatively, as shown in FIGS. 8F-H and 8J, the bottles can have a cross-shaped open internal core 840A/B (e.g., bottles 800F and 800H shown in FIGS. 8F and 8G), a star shaped open core 850 (e.g., bottle 800H shown in FIG. 8H), and/or a circular open core 860 (e.g., bottle 800K shown in FIG. 8J). Some embodiments may also have indents 820 on the external surface to increase the external surface area (e.g., bottles 800C and 800D shown in FIGS. 8C and 8D) and/or vanes/fins 830 similar to those described above (e.g., bottle 800E shown in FIG. 8E).

Figure 9:
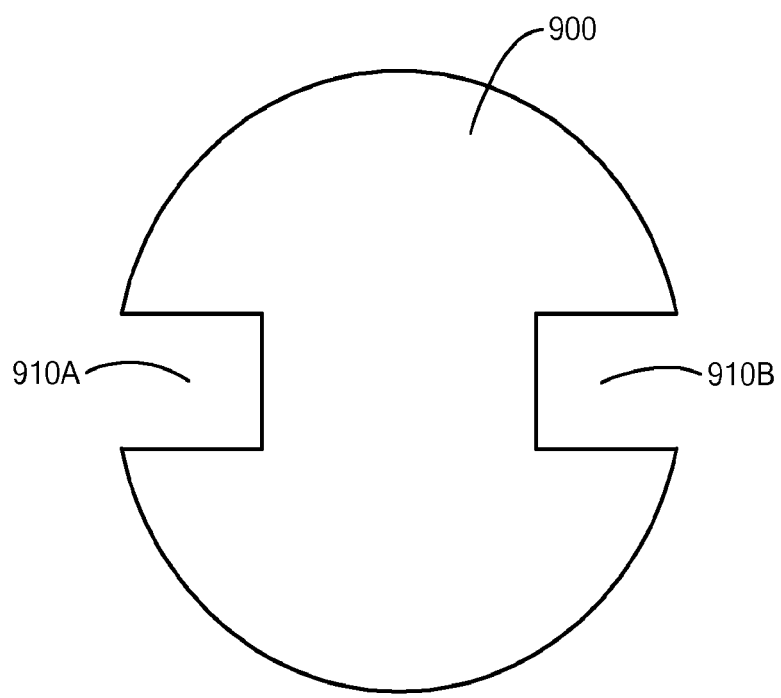
FIG. 9 schematically shows a cross-sectional view of an additional alternative embodiment of a blood component cooling and/or freezing container in accordance with further embodiments of the present invention.

FIG. 9 shows an additional alternative embodiment of a blood component cooling and/or freezing container 900 that has indents 910A/B located on either side of the bottle 900. Like the vanes 350 described above, the indents 910A/B increase the external surface area of the bottle and/or decrease the distance to the center of the bottle 900. As discussed above, this, in turn, decreases the time required to fully freeze the plasma and decreases the degradation of the plasma.

It should be noted that, in addition to decreasing the overall time required to fully freeze the plasma, the features (e.g., vanes, slits, indents, cross-sectional shapes, etc.) described above, in some embodiments, may also act to decease the time required to thaw/defrost the frozen plasma stored in the bottle. For example, the increased external surface area and/or decreased distance to the center of the bottle created by the vanes, slits, indents, etc., improve the heat exchange between the bottle and the atmosphere, and enable deeper heat penetration. This, in turn, may enable efficient and faster defrosting and allows the frozen plasma slug to release better.

As mentioned above, one of the factors that impacts the collected plasma and the degradation of the various components of the plasma (e.g., Coagulation Factors such as Factor V and Factor VIII) is temperature. To that end, because various embodiments of the present invention greatly reduce the time required to fully freeze and/or defrost the plasma contained within the blood component cooling container(s), degradation of the plasma components can be significantly reduced/minimized. This, in turn, has a beneficial impact on the recovery of selected components of the plasma (e.g., Factor V and Factor VIII) and increased yield therein.

It is important to note that, although the above described embodiments are being used to store and cool/freeze plasma, other embodiments of the present invention may be used to store and cool/freeze other blood derived fluids. For example, some embodiments may be used to store and cool/freeze red blood cells, white blood cells, platelets, or other blood components.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A blood component cooling container comprising:
   a body portion having an axial length, a proximal end and a distal end and defining an interior volume, the body portion including,
   a plurality of cooling vanes, each extending along a majority of the axial length of the body portion and radially outward from the body portion, the plurality of cooling vanes increasing the external surface area of the blood component cooling container and defining a vane internal volume; and
   an opening within the body portion configured to receive collected plasma, the opening being located at or near the proximal end;
   wherein the blood component cooling container is tapered from the distal end to the proximal end, such that a diameter of the proximal end is greater than a diameter of the distal end; and wherein the blood component cooling container has a generally frustum shape, wherein the blood component cooling container is configured to be opened with an automatic bottle opener.

2. A blood component cooling container according to claim 1, wherein the plurality of cooling vanes includes four cooling vanes.

3. A blood component cooling container according to claim 1, wherein the plurality of cooling vanes includes five cooling vanes.

4. A blood component cooling container according to claim 1, wherein the plurality of cooling vanes includes six cooling vanes.

5. A blood component cooling container according to claim 1, wherein the plurality of cooling vanes includes eight cooling vanes.

6. A blood component cooling container according to claim 1, wherein the plurality of cooling vanes includes twelve cooling vanes.

7. A blood component cooling container according to claim 1, further comprising:
a flexible metallic frame located on the external surface of the blood component cooling container, the flexible metallic frame improving the heat exchange properties of the blood component cooling container.

8. A blood component cooling container according to claim 7, wherein the flexible metallic frame contacts a bottom and at least a portion of a side of the blood component cooling container.

9. A blood component cooling container according to claim 1, wherein each of the plurality of cooling vanes are curved such that the blood component cooling container has the generally frustum shape.

10. A method of storing plasma comprising:
introducing plasma into a blood component cooling container, wherein introducing the plasma into the blood component cooling container includes transferring plasma from a blood component separation device of a plasmapheresis system to the blood component cooling container, the blood component cooling container including:
a body portion having an axial length, a proximal end and a distal end and defining an interior volume, the body portion including,
a plurality of cooling vanes, each extending along a majority of the axial length of the body portion and radially outward from the body portion, the plurality of cooling vanes increasing the external surface area of the blood component cooling container and defining a vane internal volume, and
an opening within the body portion configured to receive the plasma, the opening being located at or near the proximal end;
wherein the blood component cooling container is tapered from the distal end to the proximal end, such that a diameter of the proximal end is greater than a diameter of the distal end; and
wherein the blood component cooling container has a generally frustum shape, wherein the blood component cooling container is configured to be opened with an automatic bottle opener; and
transferring the blood component cooling container to a freezer, the plurality of cooling vanes reducing the freezing time of the plasma within the blood component cooling container;
removing the blood component cooling container from the freezer;
defrosting, at least partially, the blood component cooling container, the plurality of cooling vanes reducing the defrosting time of the plasma within the blood component cooling container;
opening the blood component cooling container using the automatic bottle opener; and
removing the plasma from the blood component cooling container, the taper preventing frozen plasma from getting stuck inside the blood component cooling container.

11. A method according to claim 10, wherein the plurality of cooling vanes includes four cooling vanes.

12. A method according to claim 10, wherein the plurality of cooling vanes includes five cooling vanes.

13. A method according to claim 10, wherein the plurality of cooling vanes includes six cooling vanes.

14. A method according to claim 10, wherein the plurality of cooling vanes includes eight cooling vanes.

15. A method according to claim 10, wherein the plurality of cooling vanes includes twelve cooling vanes.

16. A method according to claim 10, wherein the blood component cooling container includes:
a flexible metallic frame located on the external surface of the blood component cooling container, the flexible metallic frame improving the heat exchange properties of the blood component cooling container.

17. A method according to claim 16, wherein the flexible metallic frame contacts a bottom and at least a portion of a side of the blood component cooling container.

18. A blood component cooling container comprising:
a body portion having an axial length, a proximal end and a distal end and defining an interior volume;
at least one convection member spaced about the body portion, the at least one convection member increasing the external surface area of the blood component cooling container, wherein the at least one convection member includes at least one indent within the body portion extending along a majority of the axial length of the body portion; and
an opening within the body portion configured to receive collected plasma, the opening being located at or near the proximal end;
wherein the blood component cooling container is tapered from the distal end to the proximal end, such that a diameter of the proximal end is greater than a diameter of the distal end; and
wherein the blood component cooling container has a generally frustum shape, wherein the blood component cooling container is configured to be opened with an automatic bottle opener.

19. A blood component cooling container according to claim 18, further comprising:
a flexible metallic frame located on the external surface of the blood component cooling container, the flexible metallic frame improving the heat exchange properties of the blood component cooling container.

20. A blood component cooling container according to claim 19, wherein the flexible metallic frame contacts a bottom and sides of the blood component cooling container.

21. A blood component cooling container according to claim 18, wherein the at least one indent includes at least one slit within the body portion.

* * * * *